United States Patent [19]

Wohltjen

[11] Patent Number: 4,759,210

[45] Date of Patent: Jul. 26, 1988

[54] APPARATUS FOR GAS-MONITORING AND METHOD OF CONDUCTING SAME

[75] Inventor: Henry Wohltjen, Burke, Va.

[73] Assignee: Microsensor Systems, Inc., Fairfax, Va.

[21] Appl. No.: 871,694

[22] Filed: Jun. 6, 1986

[51] Int. Cl.$^4$ .......................................... G01N 31/06
[52] U.S. Cl. ........................................ 73/23; 422/88
[58] Field of Search ............... 73/23, 863.11, 863.12, 73/23.1; 340/632; 324/71.1 R; 55/205, 179; 422/88

[56] References Cited

U.S. PATENT DOCUMENTS

| | | | |
|---|---|---|---|
| 3,068,402 | 12/1962 | Redhead | 324/467 |
| 3,164,004 | 1/1965 | King | 73/23 |
| 3,174,325 | 3/1965 | Redhead | 73/23 |
| 3,338,087 | 8/1967 | Moberg et al. | 73/23 |
| 3,537,237 | 11/1970 | Gardner | 55/67 |
| 3,566,672 | 3/1971 | Carlon | 73/23 |
| 3,640,624 | 2/1972 | Anderson et al. | 356/36 |
| 3,769,837 | 11/1973 | Kraus et al. | 73/23 |
| 3,803,900 | 4/1974 | Maillard | 73/23 |
| 3,831,432 | 8/1974 | Cox | 73/23 |
| 3,897,679 | 8/1975 | Guild | 73/23.1 |
| 3,950,980 | 4/1976 | Braun et al. | 73/23 |
| 3,967,928 | 7/1976 | Schmidt et al. | 436/59 |
| 4,040,805 | 8/1977 | Nelms et al. | 55/158 |
| 4,302,422 | 11/1981 | Takahashi | 422/88 |
| 4,312,228 | 1/1982 | Wohltjen | 73/597 |
| 4,327,575 | 5/1982 | Locker | 73/23 |
| 4,347,732 | 9/1982 | Leary | 73/23 |
| 4,451,816 | 5/1984 | Ball | 338/34 |
| 4,541,268 | 9/1985 | Odernheimer | 73/23 |
| 4,542,640 | 9/1985 | Clifford | 73/23 |
| 4,580,440 | 4/1986 | Reid et al. | 73/23 |

OTHER PUBLICATIONS

Kindlund, A. et al., "Quartz Crystal Gas Monitor with Gas Concentrating Stage", Sensors and Actuators, 6 (1984), pp. 1–17.

Carey et al., "Selection of Adsorbates for Chemical Sensor Arrays by Pattern Recognition", Anal. Chem., 1986, 58, 149–53.

Primary Examiner—Michael J. Tokar
Assistant Examiner—Hezron E. Williams
Attorney, Agent, or Firm—Curtis, Morris & Safford

[57] ABSTRACT

The invention relates to method of monitoring a gas, which comprises simultaneously flowing said gas through a plurality of means for trapping gaseous species, each of said trapping means being adapted so that its selectivity in trapping of gaseous species differs from such selectivity of the other means in said plurality; subjecting each means of said plurality to conditions effecting release of any gaseous species trapped thereby while maintaining the other means of said plurality in a condition suitable for said selective trapping of gaseous species; contacting the gas issuing from each of said plurality of trapping means with each of a plurality of means for sensing said gaseous species, each said sensing means being adapted so that its selectivity to sensing said gaseous species differs from such selectivity of the other sensing means; and to apparatus for carrying out the method.

27 Claims, 1 Drawing Sheet

APPARATUS FOR GAS-MONITORING AND METHOD OF CONDUCTING SAME

FIELD OF THE INVENTION

The present invention relates to the monitoring of gas (as used herein the term "gas" refers broadly to both gases composed of only one chemical element or compound, and/or gaseous mixtures composed of more than one element and compound), and more particularly to the detection and identification of various gaseous species in the gas being monitored, as well as to the determination of whether or not such gaseous species are present in such gas.

BACKGROUND OF THE INVENTION

The detection of gases and vapors at low concentrations is often difficult due to limitations in the sensitivity of detector devices and measurement instruments. The process of detecting gases and vapors at low concentrations can be greatly enhanced if the gas or vapor can be concentrated prior to detection. Concentration of toxic materials, contaminants or other substances involving the utilization of a sorbent material which selectivity sorbs and desorbs the toxic material, contaminants, etc. is, in and of itself, known in the art. Typically, upon desorption the toxic substance, contaminant, etc. is then conducted to a sensor device or measurement instrument which registers the presence of the contaminant.

One example of such chemical measurement technology is gas chromatography. In this technique, vapors present in a flowing stream of carrier gas are forced to flow through a tube, the wall of which is coated with a sorbent material. The vapors absorb and desorb from the coating as they migrate through the tube. Usually, vapors of different chemical composition spend different amounts of time absorbed into the coating with the result that the vapors are desorbed at different times, and thus exit the tube after different elapsed times. This can afford extremely good selectivity in separating chemical compounds having similar physical and chemical properties. Furthermore, the vapors elute from the tube in a brief pulse. Thus, a detector positioned at the outlet of the tube is subjected to a sudden change in concentration of the vapor in question which is easily discriminated from slow detector signal variations (known as "drift") caused by temperature changes, impurities in the carrier gas, etc. However, the gas chromatographic approach to enhancing detection selectivity is rather disadvantageous in that a significant amount of time must be allowed for all of the vapors to elute from the tube and thus be detected, one following the other. Gas chromatography affords selectivity, but unfortunately by detecting and analyzing in a time-serial fashion, which is very time-consuming.

In a paper entitled "Quartz Crystal Gas Monitor With Gas Concentrating Stage", Kindlund, A., Sundgren, H., and Lundstrom, Ingemar; *Sensors and Actuators*, 6 (1984) pp. 1-17, there is described a recent alternative development. A coated channel is placed ahead of a sensor. Gases are collected on the channel's coating and thin thermally desorbed to improve sensor selectivity, sensitivity and drift performance. However, the apparatus described by the authors uses a single preconcentration channel, and only a single sensor. Thus, as with gas chromatography, chemical selectivity is achieved in a time-serial fashion, which is disadvantageous. Additionally, the apparatus described in the above-mentioned article was physically quite large; a Peltier element was employed in association with the preconcentration channel to provide heating and cooling for the purposes of effecting desorption of collected gases. This approach is accordingly further disadvantageous in that it requires the consumption of a substantial amount of power.

Chemical sensors, especially chemical microsensors, potentially afford many attractive features to the art such as low cost, high sensitivity, ruggedness and (in the case of microsensors) small size. These features are important in many applications. In certain embodiments, these chemical sensors are being utilized in combination with one another to make up an array of sensors. Tis array of sensors can be coupled to a pattern recognition processor to enhance the operational selectivity of the sensor system. These pattern recognition processor systems employ a pattern recognition algorithm to analyze data fed to the processor from the array of sensors when those sensors come in contact with chemical species which it is desired to detect. The analysis of information obtained from such chemical sensors with a pattern recognition processor using a pattern recognition algorithm as an analysis technique is described for example, in *Pattern Recognition Principals*, Tou, J. T., Gonzalez, R. C., Addison-Wesley, Redding, Mass. (1974); *The Interpretation of Analytical Chemical Data by Use of Cluster Analysis*, Massart, D. L., Kaufman, L. John Wiley, New York, New York (1983); Carey W. P., Beebe, K. R., Kowalski B. R., Illman, D. L., Hirschfeld, T., *Analytical Chemistry*, 1986, Vol. 58, p. 149 et seq. Nevertheless, as can be seen from the foregoing discussion, to date the art has not taken appropriate advantage of this powerful analytical tool in the monitoring of gas, and detection and identification of gas species which may be present in said gas.

OBJECTS OF THE INVENTION

It is an object of the invention to provide apparatus and a method for monitoring gas to determine whether or not such gas contains various gaseous species of interest.

It is yet another object of the present invention to provide apparatus and a method with a high degree of selectivity in respect of gas species included in a gas to be monitored.

It is yet another object of the present invention to provide apparatus and a method having the ability to detect very small amounts of gas species of interest in a gas to be monitored.

It is still another object of the present invention to provide apparatus and a method which concentrates certain gas species, when present in a gas to be monitored, to a high degree prior to contacting the gas with means for sensing such gas species.

It is a further object of the present invention to confer a high degree of effectiveness in the detection and identification of gaseous species of interest, when they are present in a gas to be monitored, by providing an increased amount of chemical information about the gas to be monitored, especially when detection and identification of the gaseous species is carried out with the use of pattern recognition techniques.

STATEMENT AND ADVANTAGES OF THE INVENTION

In one of its aspects, the present invention relates to apparatus for monitoring a gas, which comporises a plurality of means for trapping gaseous species, each of said trapping means being adapted so that its selectivity to trapping of gaseous species differs from such selectivity of the other means in said plurality, said plurality of trapping means being disposed for flow of said gas through each of said means simultaneously; in operative association with each of the trapping means, means for selectively effecting the release of trapped gaseous species therefrom; and a plurality of means for sensing any of said gaseous species released from said means for trapping each of said sensing means being adapted so that its selectivity to sensing said gaseous species differs from such selectivity of the other sensing means, each of said sensing means in said plurality being disposed for contact with said gas issuing from each of the plurality of said means for trapping.

In another of its aspects the present invention relates to a method of monitoring a gas, which comprises simultaneously flowing said gas through a plurality of means for trapping gaseous species, each of said trapping means being adapted so that its selectivity in trapping of gaseous species differs from such selectivity of the other means in said plurality; selectively subjecting each means of said plurality to conditions effecting release of any gaseous species trapped thereby, while maintaining the other means of said plurality in a condition suitable for trapping the gaseous species to which they are selective; contacting the gas issuing from said plurality of trapping means with each of a plurality of means for sensing said gaseous species, each said sensing means being adapted so that its selectivity to sensing said gaseous species differs from such selectivity of the other sensing means.

The present invention is useful in the monitoring of gases to detect whether or not they contain various gaseous species of interest, as well as for the purpose of detecting and identifying various constituents of a gas to be monitored. For instance, the invention is well suited for use in process control and environmental monitoring applications.

As evident from the foregoing, substantial advantages accrue with the practice of the present invention. The use of a plurality of trapping means and a plurality of sensing means, the output of each trapping means being contacted with each sensing means, enables the invention's practitioner to achieve a large increase in the amount of chemical information outputted by the sensing means. This is important, especially if modern computerized pattern recognition techniques are employed to process and analyze the signals provided by the sensing means, since an increase in selectivity to the various gaseous species of interest and hence the reliability and accuracy of the detection and identification of gaseous species of interest can be improved by providing an increased amount of chemical information from the plurality of sensing means. However, those increases are not obtained at the expense of sacrificing the invention's operational advantages (such as flexibility and relative quickness) in determining what (if any) gaseous species of interest are present, along with their identification, as would contrastingly be the case when using the gas chromatographic techniques described previously herein, or the preconcentrator and sensor system disclosed in the Kindlund et al. paper also mentioned above.

It is a further and substantial advantage that with the practice of the invention one achieves a high degree of collection efficiency of gas species of interest. This accrues because each means for trapping gas species can be maintained in its trapping mode during passage of the gas through the means, except for the time when it is subjected to conditions causing release of the concentrated gas species trapped thereby. This results in the concentration of any trapped gaseous species, since each such speries to which the trapping means is selective continues to be accumulated all during the passage of gas through the trapping means (except when release conditions are applied). During release time for such trapping means, the gas to be monitored is still passing through other in the plurality of the trapping means provided in accordance with the invention so that the gaseous species selectively collected therein are being trapped, and thereby concentrated, without disturbance. Accordingly, utilization of each trapping means to collect and concentrate the gas species to which it is selective is maximized for any particular period of time during which the invention is being practiced. This means that the invention is particularly effective in permitting the detection and identification of gaseous species present in very small amounts, since, due to the enhanced collection efficiency described above, these small amounts can be trapped and concentrated to a feasibly high degree. This is accomplished without the necessity to expend large amounts of time concentrating gas species and waiting for them to desorb or elute as would be necessary with use of the gas-chromatographic and the Kindlund et al. techniques described above (which obtain selectivity in time-serial fashion).

The present invention, including further objects, features and advantages thereof, will be more fully understood from the following description of certain preferred embodiments, when read with reference to the accompanying drawings.

DESCRIPTION OF CERTAIN PREFERRED EMBODIMENTS

Figure 1:
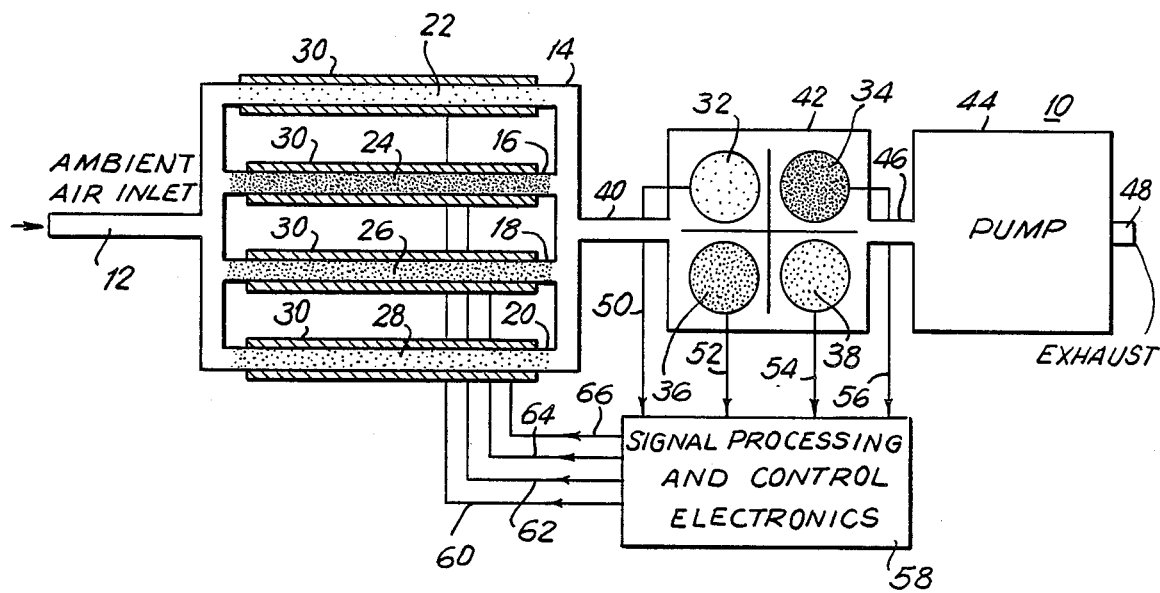
FIG. 1 is a schematic view of apparatus in accordance with the present invention.

In several advantageous embodiments the invention lends itself to use with a wide variety of trapping means and sensing means. Because of this flexibility, the invention is adaptable to miniaturization, with concomitant savings in cost to operate and in convenience of use in space-limited applications or in applications requiring portability.

More specifically, each trapping means typically includes a component such as a tube or other conduit through which gas to be monitored is passed. The trapping means also includes a sorbent mass disposed so as to intercept the gas passing through such means. According to the present invention a plurality of such trapping devices is typically arranged in an array so that gas to be monitored flows through each simultaneously. The arrangement of the devices can be such that they are placed in substantial parallel relationship with one another; however, alternative configuration are suitable as long as the arrangement of the devices flow of the gas therethrough in accordance with the practice of the invention as herein described. Once equipped with the teachings herein, one of ordinary skill in the art will be capable of selecting an appropriate arrangement of the plurality means for trapping, and thereby concentrating, gas species to fit his needs.

The sorbent mass is any suitable material which is selective to sorption of one or more gaseous species consistent with the practice of the present invention. Such sorbent materials, in and of themselves, are well known in the art. Examples of sorbent materials which are suitable for practice of the present invention are activated charcoal, alumina, zeolite molecular sieves, metals such as transitions metals and especially metals of group Ib and group VIII of the periodic table (examples of suitable metals are iron, copper, titanium, tungsten, nickel, gold, silver, platinum and palladium) silica gels, and polymeric sorbents. There are many suitable polymeric sorbent materials which are well-known to those of ordinary skill in the art for use in connection with, for example, gas-chromatographic techniques. Illustratively, sorbent materials such as those commercially available under the name "Tenax" are useful; these are derivatives of 2,6-diphenyl-p-phenylene oxide.

Also, materials commercially available under the name "Porapak" are suitable; these are a family of styrene divinyl benzene polymers, ethyl vinyl and divinyl benzene polymers, vinyl pyrrolidone polymers and vinyl pyridine polymers. Additionally suitable are materials commercially available under the name "Chromosorb"; these are a family of styrene divinyl benzene polymers, cross-linked polystyrene, polyacrylonitrile and cross-linked acrylic esters.

The sorbent material placed in each of the plurality of trapping devices is advantageously chosen so that its selectivity to sorption of gaseous species in the gas to be monitored is different from that of sorbent used in each of the other trapping devices utilized. The selectivity characteristics of the various sorbent materials which can be utilized in accordance with the invention are generally well-known in the art. In any case, these characteristics can be determined empirically by the practitioner of the invention without undue experimentation and through the exercise of routine skill of the art, especially in light of the predetermination of gaseous species which the practitioner seeks to detect or anticipates may be present in the gas to be monitored.

The sorbent material is generally located in an interior portion of the trapping device. It is employed in an amount sufficient so as to effect a degree of concentration of the gas species to which the sorbent is selective (should such gas species be present) which will permit detection and identification by downstream sensing means in accordance with the principles of the invention. Determination of the amount of sorbent to be used may involve taking into account the magnitude of the sampling period, i.e., the time period of gas flow through the device prior to subjecting of the device to conditions which will cause its releasing of any gas species concentrated thereby. Other factors which (in view of the teachings herein) will be apparent to one of ordinary skill in the art, such as the velocity of gas flow through the trapping device, may also have an effect on the amount of sorbent which is advantageously exposed to the gas as it flows through the trapping device—and thus the amount of sorbent material which is located in the interior of the device. These factors will be readily determinable by one of ordirary skill in the art equipped with the knowledge of my invention which can be derived herefrom.

In accordance with the foregoing, the sorbent material is suitably coated or otherwise disposed on at least a part of an interior surface of the trapping device, particularly if that device is a tube or other conduit. Alternatively, the interior space of the device (or some portion of it) is suitably packed with sorbent-containing material. Illustratively, the packing material can be the sorbent itself, in the form of powder or fibers. In other embodiments of the invention, the packing material is sorbent deposited on a powder of inert carrier material or a mesh or fiber mass of inert carrier material. It is, of course, readily understandable that the arrangement of the sorbent mass in the trapping device should permit relatively free passage of the gas through the device while at the same time promoting sufficient contact between gas and sorbent material to ensure adequate collection of the gas species of interest, should they be present in the gas being monitored.

Ordinarily, during gas flow through the trapping means, conditions are maintained such that the sorbent material can sorb (either adsorb or absorb) one or more gas species of interest should such species be present on the gas to be monitored. Normally, this operation would be carried out at room temperature and pressure, but other conditions under which gas species if present can be sorbed are also suitable (although this may cause some change in collection efficiency).

The release of any collected gas species is effected by subjecting the trapping device, and particularly the sorbent material therein, to conditions which result in a desorption of the gas species which have been trapped and concentrated in the material. Typically that release is effected by heating the trapping device, and therefore the sorbent material therein, to effect a thermal desorption of the gaseous species. (Desorption, for example, could also be effected by changes in pressure.) This is advantageously accomplished by placing the trapping device in proximity of a heating element, for instance a resistive heating element, so that when the heating element is operative it causes release of the collective gaseous species from the sorbent material. As will be appreciated, the sorbent materials are chosen in such embodiments for their characteristic desorption in response to heating. The capacity of the heating element to impart heat energy is advantageously chosen to be sufficient to effect a rapid release of the collected gaseous species trapped in the sorbent material so that the released gaseous material is carried in a correspondingly concentrated form to the sensors which are "downstream" of the trapping devices, rather than being diluted due to a gradual release from the sorbent material so that the gaseous material arrives at the sensors in a more diffuse form which makes detection and identification more difficult. Accordingly, the sorbent material and the heating element to be used in connection with it are advantageously matched such that the desorption conditions required by that material will be met by the capacity of the heating element to supply heat energy to the sorbent material.

The heating element itself is advantageously a thin-film resisrance heater which is deposited (e.g. by Coating) on at least a part of the exterior of each trapping device, especially when the device is a tube or other conduit. The thin-film resistance heater is advantageously a resistive ink is coated on an exterior portion of the trapping device. Such resistive inks typically comprise a glass matrix or an organic matrix in which matrix are incorporated particles of one or more metals or alloys, inert carrier particles which are coated by one or more pure or alloy metals, or a combination thereof (though other kinds of resistive inks which are consistent with the practice of the invention as described herein are also suitable). These resistive inks are commercially available. and are well-known to one of ordinary skill in the art. They are applied to the trapping device's exterior, for instance, in the form of a "paste" having suitable rheological properties so that it flows sufficiently to permit the coating operation. In the case of resistive ink heating elements having a glass matrix, the paste is typically made up of the metal-containing particles, glass frit (or other glass particles), and an organic vehicle to impart the aforementioned rheological properties. The paste is fired (heated) to sufficient temperature after coating on the trapping device to fuse the glass particles; the organic vehicle is driven off during the firing operation. In the case of resistive ink heating elements having an organic matrix, the paste does not contain glass particles but rather is typically formed of an organic resin or other suitable organic binder material (optionally with one or more additional organic vehicles) and the metal-containing particles. The matrix is formed after application of the paste to the trapping device by subjecting the paste to appropriate curing conditions (such as irradiation, air-drying, etc.).

Alternatively, the resistance heating element can be a thin layer of an appropriately resistive metal which is applied to at least part of the exterior of each trapping device. The thin layer can be a coating of a appropriate metal, such as aluminum, gold, nickel or platinum. Another manner in which to impart sufficient heat energy to the sorbent material to accomplish thermal desorption is to form the resistance heating element of a wire coiled around an exterior portion of the trapping device. The wire is made of an appropriately resistive metal as well.

In each of the foregoing cases, heating is effected by passing current through the resistive heating element. It is within the skill of the art (once the skilled worker is equipped with the teachings herein) to predetermine the resistance, and the heating capacity due to that resistance, which will be suited to cause the desorption of the trapped gaseous species from the sorbent material; this can be ascertained empirically without undue experimentation. In the foregoing connection, it is noted that a resistance heating element formed of a resistive ink exhibits a characteristically high resistance which is better suited for use with high voltage, lower current sources. On the other hand, a thin metal film, such as a thin gold film, typically has a lower resistance (for example a few ohms). A resistant heating element made of a metal film or layer can be effectively driven by a low voltage, high current source, features which are characteristic of a portable power source, such as a battery. With respect to the aforementioned metal-film-resistance heating element, it will further be appreciated that in certain advantageous embodiments its use permits enhanced control of heating conditions causing desorption. Generally speaking thermal desorption conditions are generated by and controlled through regulation of the power input to the heater; the power supplied to the heating element is that which has been predetermined to produce a desired amount of heat to effect thermal desorption. However, if one employs a film or layer of a metal whose temperature coefficient of resistance is known, than the heating element itself can be used as a temperature sensor. By monitoring the temperature of the metal film or layer, and relaying that information by means of appropriate circuitry to a control unit, the system can be made to be self-adjusting so that the power supplied to the resistive heating element will be keyed to the temperature of the metal film. By this means, the temperature of the metal film can be used as a basis upon which to increase or decrease power so as to maintain the heating input to the sorbent material constant, thus improving the reproducibility of thermal desorption.

After desorption any concentrated gas species which are introduced into the flow of gas through the trapping means are passed to the downstream plurality of sensing means. The sensing means are advantageously arranged in array form so that each of the sensing means comes into contact with the gas to be monitored after it emerges from its passage through the plurality of trapping means. The sensing means advantageously comprise chemical sensors which, in and of themselves, are known to those of ordinary skill in the art. Illustratively, the means for sensing the aforementioned gas species is a piezoelectric sensor, an organic semiconductor chemiresistor, a chemically sensitive field effect transistor, a metal oxide semiconductor, or an electrochemical cell. As piezoelectric sensors it is suitable to employ, for instance, a bulk wave piezoelectric sensing device such as disclosed in King U.S. Pat. No. 3,164,004, granted Jan. 5, 1986 or a surface acoustic wave sensor device as described in Wohltjen U.S. Pat. No. 4,312,228, granted Jan. 26, 1982. The subject matter of these patents is incorporated by reference herein. In one advantageous embodiment of the invention, the portion of the sensor which is adapted for exposure to the gaseous species of interest (should they be present) is made from the same sorbent material as that which is employed is the trapping devices upstream of the plurality of sensing means. Illustrative metal oxide semiconductor sensors suitable for use in the present invention are disclosed in Clifford U.S. Pat. No. 4,542,640, granted Sept. 24, 1985; the subject matter of that patent is also incorporated by reference herein.

While chemical sensors are advantageously employed in practicing the invention, other sensors may also be utilized in some embodiments. For example, sensors based on optical phenomena—that is, spectroscopic detection apparati—such as non-dispersive infrared gas detectors—are also acceptably employed.

The sensors of the claimed invention are typically components which emit a change in output signal when they come in contact with gaseous species to be detected in accordance with the invention. Thus, when a change in chemical concentration or activity occurs at the portion of a sensor when it is exposed to the aforementioned gaseous species, this results in a change in current, frequency, voltage or some other measurable parameter. This change is an indication of the presence of the gaseous species. Contact with the entire plurality of sensing means utilized in accordance with the invention yields a set of signals (or signal changes) which can be used as a means of analyzing the chemical constituents of the gas with which the sensors have come in contact. This set signal outputs of the sensors forms a "spectrum" of information which is basis for interpretation and analysis to detect and identify gaseous species which may be present.

The signals (or spectra) from the plurality of sensing means are relayed to an appropriate processing system for the aforementioned interpretation and analysis to determine whether or not any of the gaseous species to which the trapping devices and sensors are selective is present, and if so to detect that presence and identify the gaseous species. (This is of course based on the signal output of the sensors as they come in contact with the gas being monitored; if the gas contains any of such gaseous species then one or more telltale signal output indications will be observed by the processing apparatus.)

The invention as previously described has as one of its principal and further advantages the ability to compensate for "drift" which is frequently exhibited by chemical sensors typically used to detect and identify the gaseous species generally of interest in these matters. By "drift" is meant a change in output signal from the sensing means resulting from the effects of temperature, pressure or other uncontrolled influences over a relatively long period of time. The problem of drift is somewhat endemic to the use of systems in which sensors are utilized to obtain chemical information about a gas to be monitored. The drift, or change in output signals, of those sensors over a relatively long period of time is significant if the detection and identification of chemical or gaseous species requires employment of signal outputs taken on a relatively long-term basis, since a component of any change in the signal can be due to extraneous drift phenomena and have nothing to do with detection of gaseous species to which the sensor is selective. This introduces inaccuracy. However, with the present invention sensor drift can be compensated for without sacrificing the other advantages of the invention. This is because the present invention is readily adapted to a mode in which the signal from the sensing means can be measured at a time when none of the trapping means is being subjected to release or desorption conditions, thereby to obtain a base signal corresponding to the absence of any gas species to be detected and identified. Shortly thereafter, when one of the means for trapping gas species is deliberately subjected to release (e.g., desorption) conditions another measurement of the output signal of the sensing means can be obtained before a sufficient amount of time has passed for the drift phenomenon to have introduced an extraneous change in the signal (not related to detection of a gas species) relative to the base signal. The time difference between measurement of the base signal and measurement of the output signal corresponding to passage of the gas containing any gaseous species desorbed from the trapping means subjected to desorption conditions is insignificant compared to the time required for the output signal of the sensing means to be affected by drift. By continually measuring the difference between a "fresh" base signal and a signal obtained shortly thereafter corresponding to sensor-contact with gas containing any gaseous species of interest desorbed from a trapping means subjected to release conditions, any change in signel due to a drift phenomenon over a long period of time is cancelled out, thus compensating for the drift and removing any inaccuracy which might otherwise be introduced by comparison of signals which are no longer normalized.

One of the principal and essential features of the present invention is that the output of all of the trapping devices employed in accordance with it is contacted with each and every of the sensing means utilized. This produces a spectrum of signals for interpretation based on the contact of all of the sensors with the output of each of the trapping devices during the time it is subjected to desorption (or other release) conditions. The amount of chemical information about constituents of the gas being monitored is dramatically increased by using this arrangement; the amount of chemical information about the gas being monitored is, as will readily be appreciated, a function not just of the number of sensors, but rather of the product of the number of sensors times the number of trapping devices, the output from each of which is contacted with each of the sensors. As will further be appreciated, the amount of chemical information which can be obtained with the system increases even more dramatically as the number of trapping devices and/or sensors is increased.

In connection with the foregoing, a particularly advantageous processing system with which to use the invention is a computerized pattern recognition processor. This type of processor is based on the utilization of a pattern recognition algorithm, the accuracy and reliability of which in analyzing the output of signals of the associated sensors is substantially increased with an increase in the amount of chemical information (e.g., the number and information content of signal spectra) received from such sensors. As discussed above, practice of the present invention increases the amount of chemical information which is yielded by the plurality of sensing means. Thus, use of the present invention in conjunction with pattern recognition techniques confers a high degree of accuracy and reliability in the detection and identification of any gaseous species of interest in the gas being monitored, without sacrificing other advantages over alternative systems as discussed previously.

Figure 2:
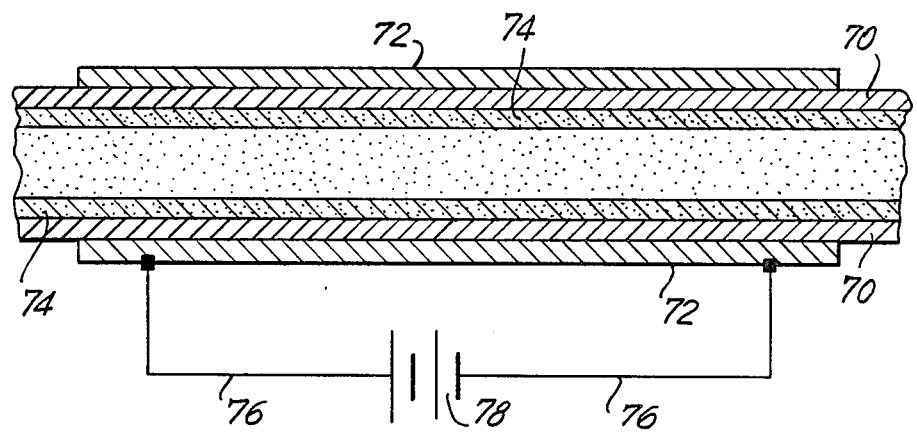
FIG. 2 is a schematic view of one embodiment of gas species-selective trapping and concentrating means utilized in accordance with the present invention.

Apparatus in accordance with the invention is depicted in FIGS. 1 and 2. FIG. 1 shows a system 10 for concentrating, detecting and identifying any gaseous species of interest (e.g., contaminants, toxic substances or the like) which may be present in a gas to be monitored, in this case ambient air. The system includes an ambient air inlet tube 12 which is connected to each of thin-walled tubes 14, 16, 18 and 20 (each tube is 2 cm in length and has an inside diameter of 0.25 mm and an outside diameter of 0.35 mm), in this case made of fused silica, and adapted for concentration and release (under appropriate conditions) of certain of the aforementioned gas species in accordance with the invention. Tubes 14, 16, 18 and 20 are packed with gaspermeable beds of powdered sorbent material 22, 24, 26 and 28, respectively. Additionally, each of tubes 14, 16, 18 and 20 is equipped with a thin film resistance heater 30, coated directly on the tube. Each of sorbent materials 22, 24, 26 and 28 is chosen so that its selectivity to gaseous species of interest which may be present in the ambient air differs from the selectivity to such species of the other three sorbent materials. Each of tubes 14, 16, 18 and 20 communicates with sensors 32, 34, 36 and 38 via tube 40. The sensors themselves are piezoelectric sensor components which are coated with sorbent materials; the sorbent: materials used in beds 22, 24, 26 and 28 correspond to the sorbent materials used in sensors 32, 34, 36 and 38, respectively. The compartment 42 in which the array of sensors 32, 34, 36 and 38 is housed communicates with pump 44 via tube 46. Pump 44 operates to ambient air into the system through inlet tube 12 and expels air which has already passed through the system at exhaust 48. As can be seen from lines 50, 52, 54 and 56, the above-discussed sensors are connected by appropriate circuitry to a signal processing and control electronics unit 58. Unit 58 includes a pattern recognition processor which employs a pattern recognition algorithm to detect and identify any gas species of interest which are in the ambient air drawn into the system at tube 12. As is further shown by lines 60, 62, 64 and 66, power is supplied to thin film resistance heaters 30 by unit 58. This power is provided on an intermittent basis so that only one of the thin film resistance heaters is operative at any one time.

FIG. 2 is an enlarged schematic illustration of a trapping device utilized in accordance with the claimed invention. Tube 70 is coated on part of its exterior surface with a thin film resistance heater 72 made of a metal film, in this case gold. Material 74 is coated on the inner wall of tube 70; material 74 selectively absorbs one or more gaseous species which may be present in a gas which is passed through tube 70 when it is incorporated in a system such as that illustrated in FIG. 1. As shown by lines 76, power supply 78 is connected to thin film resistance heater 72 to supply current to the resistance heater thereby generating heat to effect a thermal desorption of any gas species trapped and concentrated by selective coating 74.

In operation, ambient air is drawn through tube 12 (by the action of pump 44) into each of tubes 14, 16, 18 and 20. In those tubes the ambient air passes through packed sorbent materials 22, 24, 26 and 28, respectively. Due to the differing selectivity characteristics of those sorbent materials, contaminants (gas species) present in the ambient air are selectively trapped by one or more of the sorbent materials. The selectivity of each sorbent material is determined by its chemical composition. After a brief sampling period (e.g. one minute during which the sensors provide a base-line signal) each tube 14, 16, 18 and 20 is successively individually heated (e.g. for a period of 2-3 seconds with a period of 10 seconds between heating cycles of the individual tubes), one after another, by operation of the thin film resistance heater 30 on the tube. The sequence and timing of heating by each of thin film resistance heaters 30 is determined by control unit 58. The heating of the tube causes a thermal desorption of any gas species of interest in the ambient air initially, which were then sorbed by any of materials 22, 24, 26 and 28. Thus, when tube 14 is heated any gas species sorbed by material 22 are then desorbed while ambient air continues to pass through each of tubes 16, 18 and 20; of course, ambient air is passed through material 22 and tube 14 during desorption as well. The desorbed gas species are then combined with ambient air flow emerging from each of tubes 14, 16, 18 and 20, passed through tube 40 and contacted with the array of sensors 32, 34, 36 and 38. Any gas species (e.g., contaminants) which are contained in the air flow into the sensor array are then sorbed by the sorbent materials of the aforementioned sensors, particularly the sorbent material of sensor 32 which is the same as the sorbent material 22 in tube 14. Flow of this air past the array of sensors causes those sensors to output a characteristic pattern of signals which is relayed to and processed by unit 58. The desorption sequence is then repeated for each of tubes 16, 18 and 20, one at a time, until several spectra of output signals from the sensor array housed in compartment 42 have been provided to unit 58 for analysis. In each case, air passing through compartment 42 is conducted via duct 46 through pulp 44 and exhausted at tube 48.

Thus, with the present invention substantial difficulties encountered in utilizing other gas monitoring techniques are eliminated. Additionally, substantial advantages which are not necessarily achieved with alternative gas monitoring technology are attendant upon practice of the invention.

The terms and expressions which have been employed herein are used as terms of description and not of limitation, and there is no intention in the use of such terms and expressions to exclude any equivalents of the features described or of portions thereof, its being recognized that various modifications are possible within the scope of the invention.

What is claimed is:

1. Apparatus for monitoring a gas, which comprises a plurality of means for trapping gaseous species, each of said trapping means being adapted so that its selectivity to trapping of gaseous species differs from such selectivity of the other means in said plurality, said plurality of trapping means being disposed for flow of said gas through each of said means simultaneously;

in operative association with each of the trapping means, means for selectively effecting the release of trapped gaseous species therefrom; and a plurality of means for sensing any of said gaseous species released from said means for trapping, each of said sensing means being adapted so that its selectivity to sensing said gaseous species differs from such selectivity of the other sensing means, each of said sensing means in said plurality being disposed for contact with said gas issuing from each of the plurality of said means for trapping.

2. Apparatus as defined in claim 1, wherein said means for trapping gaseous species comprises a sorbent mass which selectively traps and concentrates said gaseous species under normal operating conditions and desorbs said gaseous species when heated.

3. Apparatus as defined in claim 2, wherein the sorbent mass is activated charcoal, alumina, a zeolite molecular sieve, a metal, a silica gel, or a polymeric sorbent.

4. Apparatus as defined in claim 3, wherein the polymeric sorbent is a derivative of 2,6-diphenyl-p-phenylene oxide, a styrene divinyl benzene polymer, an ethyl vinyl or divinyl benzene polymer, a vinyl pyrrolidone polymer, a vinyl pyridine polymer, cross-linked polystyrene, polyacrylonitrile or a cross-linked acrylic ester.

5. Apparatus as defined in claim 1, wherein the means for trapping gaseous species is a tube containing a sorbent material.

6. Apparatus as defined in claim 5, wherein said tube is formed of fused silica.

7. Apparatus as defined in claim 1, wherein said means for selectively effecting the release of trapped gaseous species is a heater disposed sufficiently proximately of said means for trapping gaseous species so that when said heater is operative it causes release of said gaseous species from said means for trapping same.

8. Apparatus as defined in claim 1, wherein the means for trapping gaseous species comprises a tube and the means for selectively effecting release of trapped gaseous species is a thin film resistance heater covering at least a portion of the outer wall of said tube.

9. Apparatus as defined in claim 8, wherein said resistance heater includes a resistive ink coated on at least a portion of the outer wall of said tube.

10. Apparatus as defined in claim 1, wherein said means for sensing said gaseous species is a piezoelectric sensor, an organic semiconductor chemiresistor, a chemically sensitive field effect transistor, a metal oxide semiconductor, or an electrochemical cell.

11. Apparatus as defined in claim 10, wherein said piezoelectric sensor is a bulk wave piezoelectric sensor or a surface acoustic wave sensor.

12. A method of monitoring a gas, which comprises
simultaneously flowing said gas through a plurality of means for trapping gaseous species, each of said trapping means being adapted so that its selectivity in trapping of gaseous species differs from such selectivity of the other means in said plurality;
selectively subjecting each means of said plurality to conditions effecting release of any gaseous species trapped thereby while maintaining the other means of said plurality in a condition suitable for said selective trapping of gaseous species;
contacting the gas issuing from each of said plurality of trapping means with each of a plurality of means for sensing said gaseous species, said sensing means being adapted so that its selectivity of sensing said gaseous species differs from such selectivity of the other sensing means.

13. A method as defined in claim 12, which further comprises contacting said gas with a sorbent mass included in each said means for trapping gaseous species, thereby to sorb in each said mass any gaseous species as to which the sorbent mass is selective.

14. A method as defined in claim 13, wherein the sorbent mass is activated charcoal, alumina, a zeolite molecular sieve, a metal, a silica gel, or a polymeric sorbent.

15. A method as defined in claim 14, wherein the polymeric sorbent is a derivative of 2,6-diphenyl-p-phenylene oxide, a styrene divinyl benzene polymer, an ethyl vinyl or divinyl benzene polymer, a vinyl pyrrolidone polymer, a vinyl pyridine polymer, cross-linked polystyrene, polyacrylonitrile or a cross-linked acrylic ester.

16. A method as defined in claim 12, which further comprises passing said gas through a plurality of means for trapping a gaseous species wherein each such means comprises a tube having at least a part of its inner wall coated with a sorbent mass.

17. A method as defined in claim 16, wherein said tube is formed of fused silica.

18. A method as defined in claim 12, which comprises subjecting each means for trapping gaseous species to an amount of heating sufficient to release said trapped gaseous species, the heating of said means being effected with a thin-film resistance heater disposed sufficiently proximately of said means for trapping gaseous substances as to effect said release.

19. A method as defined in claim 12, wherein said plurality of means for sensing said gaseous species comprises an array of sensors the selectivity of each sensor to said gaseous species differing from such selectivity of the other sensors.

20. A method as defined in claim 19, wherein each said sensor comprises a piezoelectric sensor, an organic semiconductor chemirestor, a chemically sensitive field effect transistor, a metal oxide semiconductor, or an electrochemical cell.

21. A method as defined in claim 20, wherein said piezoelectric sensor is a bulk wave piezoelectric sensor or a surface acoustic wave sensor.

22. Apparatus as defined in claim 1, which further comprises means for measuring a signal emitted by each of the plurality of said sensing means.

23. Apparatus as defined in claim 1, which further comprises means for measuring a signal emitted by each of the plurality of said sensing means, and control means which causes said measuring means to measure said signal just prior to contacting the sensing means with gas containing the output of one of said trapping means which has been subjected to conditions effecting release of any gaseous species trapped therein, and again causing said measuring means to measure the corresponding signal when the sensing means is contacted with said gas containing said output.

24. A method as defined in claim 12, which further comprises measuring a signal emitted by each of the plurality of said sensing means when the sensing means is contacted with the output of said trapping means which has been subjected to conditions effecting release of any gaseous species trapped therein.

25. A method as defined in claim 12, which further comprises, just prior to contacting said gas containing the output of one of said trapping means subjected to conditions effecting release of any trapped gaseous species, measuring a signal emitted by each of said sensing means, and then comparing the corresponding signal emitted by each of said sensing means when it is contacted with said gas containing said output.

26. Apparatus for monitoring a gas, which comprises an array of tubes containing a sorbent mass the selectivity of the sorbent mass in each said tube to trapping of gaseous species being different from such selectively of the sorbent mass in each of the other tubes in said array, said array of tubes being disposed in substantially parallel relationship such that there is flow of said gas through each of said tubes simultaneously;
a portion of the exterior of each of said tubes being coateed with a thin film resistance heater formed of a resistive ink; and
an array of piezoelectric sensors, each of said sensors being adapted so that its selectively to sensing said gaseous species differs from such selectivity of the other sensors, each of said sensors in said array being disposed for contact with said gas issuing from each of the array of said tubes.

27. A method of monitoring a gas, which comprises simultaneously flowing said gas through an array of tubes containing sorbent mass, the selectivity of the sorbent mass in each said tube to trapping of gaseous species being different from such selectivity of the sorbent mass in each of the other of said tubes;
successively subjecting each of the tubes of said array to conditions effecting release of any gaseous species trapped thereby while maintaining the other tubes of said array in a condition suitable for said selective trapping of gaseous species;
contacting the gas issuing from each of said array of tubes with each of an array of piezoelectric sensors, the selectivity of each said sensor to sensing said gaseous species differing from such selectivity of each of the other sensors in said array.

* * * * *